(12) United States Patent
Overes et al.

(10) Patent No.: US 10,194,969 B2
(45) Date of Patent: Feb. 5, 2019

(54) SURGICAL TORQUE LIMITER

(71) Applicant: 41medical AG, Bettlach (CH)

(72) Inventors: Tom Overes, Langendorf (CH); Robert Frigg, Bettlach (CH)

(73) Assignee: 41medical AG, Bettlach (CH)

( * ) Notice: Subject to any disclaimer, the term of this patent is extended or adjusted under 35 U.S.C. 154(b) by 338 days.

(21) Appl. No.: 14/901,600

(22) PCT Filed: Jul. 15, 2014

(86) PCT No.: PCT/CH2014/000108
§ 371 (c)(1),
(2) Date: Dec. 28, 2015

(87) PCT Pub. No.: WO2015/006880
PCT Pub. Date: Jan. 22, 2015

(65) Prior Publication Data
US 2016/0143682 A1    May 26, 2016

(30) Foreign Application Priority Data

Jul. 15, 2013    (CH) ...................................... 1256/13

(51) Int. Cl.
*A61B 17/88* (2006.01)
*B25B 23/142* (2006.01)
(Continued)

(52) U.S. Cl.
CPC ...... *A61B 17/8875* (2013.01); *B25B 23/1427* (2013.01); *A61B 2017/0046* (2013.01); *A61B 2090/031* (2016.02)

(58) Field of Classification Search
CPC .............................. A61B 17/88; A61B 17/8875
See application file for complete search history.

(56) References Cited

U.S. PATENT DOCUMENTS

| 5,655,420 | A | 8/1997 | Ogawa et al. |
| 2003/0221524 | A1* | 12/2003 | Hu ........................ B25B 23/141 81/467 |
| 2007/0283788 | A1 | 12/2007 | Kolkind |

FOREIGN PATENT DOCUMENTS

| EP | 1 854 587 A2 | 11/2007 | |
| WO | WO 2013/088158 A2 | 6/2013 | |
| WO | WO 2013088158 A2 * | 6/2013 | ........... G10D 13/023 |

* cited by examiner

*Primary Examiner* — Christopher Beccia
(74) *Attorney, Agent, or Firm* — Mu P.C.

(57) ABSTRACT

The present application relates to a torque limiter (1) comprising a handle (2) with a mono-block cylindrical handle-body. The cylindrical handle-body includes a central through bore (3) having an axis (B) at a right angle to a longitudinal axis (A) of the cylindrical handle-body as well as a first pocket (4) and a second pocket (5). The first pocket (4) is arranged on a first side and the second pocket (5) is arranged on a second side of said cylindrical handle-body opposite of said first side. The first pocket (4) and the second pocket (5) are arranged along said longitudinal axis (A) and intersect each other in the area of said central through bore (3), each of said first pocket (4) and said second pocket (5) comprising at least one magnet (6a, 6b, 7a, 7b; 35). Further, the torque limiter (1) comprises a mono-block shaft (20) having a central shaft (21) removably arranged in said central through bore (3), said central shaft (21) having a drive (23) arranged at a first end. The central shaft (21) comprises at least one protrusion (25, 26; 27) arranged at a second end and being at a right angle to a central axis (22) of said central shaft (21), said at least one protrusion (25, 26; 27) being sized and shaped to be arranged within said first pocket (4) or said second pocket (5) and to magnetically interact with the at least one magnet (6a, 6b, 7a, 7b; 35) arranged in said first pocket (4) or said second pocket (5).

20 Claims, 13 Drawing Sheets

(51) Int. Cl.
*A61B 17/00* (2006.01)
*A61B 90/00* (2016.01)

SURGICAL TORQUE LIMITER

TECHNICAL FIELD

The invention relates to a torque limiter for a surgical device.

BACKGROUND ART

Bone screws are implantable medical fixation devices used in many fields of surgery, like traumatology, spine surgery and dental surgery. For different reasons, the insertion torque is an important factor for success of the treatment. In spinal surgery for example, a maximal insertion torque is defined to prevent bone from cracking. In traumatology another reason for screw insertion with a controlled torque is the prevention of cold-welding between plates and screws, which renders implant removal impossible.

In dental applications, a too high torque indicates a not correctly prepared bone bed, which might influence osseointegration of an implant. Furthermore, often a limited torque is required such as to prevent damage to the drive in a screw or similar, such as to allow a subsequent removal of the screw or similar.

The insertion torque usually needs to be controlled to prevent a reduced performance of a medical device, either relating to its direct interaction with bone or its interaction with another medical device of a larger implant system or assembly.

To control these insertion torques, torque wrenches are available on the market. Common torque wrenches often are very complexly built, expensive and need regular calibration to guarantee the desired torque. The complexity of the existing devices often influences the cleanability of these surgical instruments. Furthermore, torque wrenches are expensive devices and most often only are designed to control one level of torque per wrench type.

As a further example, EP 1 854 587 A2 (Teleflex Medical Inc.) describes a magnetic torque-limiting device. The device comprises a first end to engage a fastener, a second end to receive an applied torque and a magnetic torque limiter to transmit the applied torque from the second end to the first end such as to rotate the first end when the applied torque is less than a predetermined limit. The device includes a pair of magnets aligned with opposing poles facing one another. When the handle is rotated, one or more lugs are brought to bear on levers. The levers include an arm to urge the magnets apart as well as an arm bearing on a lug. When the force exerted on the lugs exceeds the magnetic force, the magnets will be urged to separate by means of the levers and the torque transmitted to the first end is diminished.

WO 2013/088158 (Kennedy et al.) discloses an adjustment device comprising a handle portion, a spindle portion adapted to engage an element to be rotated against resistive torque, a first magnet arrangement comprising one or more magnets and being attached to the handle portion as well as a second magnet arrangement comprising one or more permanent magnets and being attached to the spindle portion. The distance between the first and the second magnet arrangement may be increased or decreased, whereby the magnets are arranged such that poles of one magnet arrangement are generally aligned with opposing poles of the second magnet arrangement. Hence, rotation of one of the magnet arrangements entails the rotation of the second magnet arrangement. If a pre-set torque level is reached, the magnetic attraction forces are overcome by the rotational forces, such that the entailed rotation of the magnet arrangement is stopped.

U.S. Pat. No. 5,655,420 (Ogawa et al.) describes tightening tools having a defined maximal torque such as to avoid the problem of over tightening pipe joints. The tightening tool comprises a head having a socket for an engagement portion of a threaded member, a head supporting the head rotatably about the axis of the socket and a handle integral with the head support, a magnet being attached to one of the head and the head support, while an attracted portion is provided on the other and attractable to the magnet. The position of the magnet is made adjustable such as to vary the distance between the magnet and the attracted portion.

One major drawback of the torque limiter arrangements known in the prior art is that they require different separate parts cooperating with each other, some of these parts even being movable in respect to other parts. Especially in connection with surgical instruments, such as surgical screw drivers, assemblies of different parts and movable parts may not be easily cleaned and sterilized, especially since body fluids or tissue parts may remain stuck between assembled parts or jammed under a movable part. However, insufficient cleaning and sterilization may be a serious threat to patients subsequently treated with said instruments. Further, either the torque limiter according to the prior art only have a single pre-defined torque level or the switching to a different torque level requires time-consuming manual adjustment.

SUMMARY OF THE INVENTION

It is the object of the invention to create a coupling device pertaining to the technical field initially mentioned, which allows the use of mono-block components, especially a mono-block handle and a mono-block shaft. A further objective of the present invention is to provide a coupling device allowing an easy switching of the pre-defined torque to at least two different torque levels.

The solution of the invention is specified by the features of claim 1. According to the invention, the torque limiter includes a handle with a mono-block cylindrical handle-body, said cylindrical handle-body comprising a central through bore having an axis at a right angle to a longitudinal axis of the cylindrical handle-body. Further, the cylindrical handle-body includes a first pocket and a second pocket, said first pocket being arranged on a first side and said second pocket being arranged on a second side of said cylindrical handle-body opposite of said first side, the first pocket and the second pocket being arranged along said longitudinal axis and intersecting each other in the area of said through bore, each of said first pocket and said second pocket comprise at least one magnet. The torque limiter further includes a mono-block shaft having a central shaft removably arranged in said central through bore, said central shaft having a drive arranged at a first end. The shaft further comprises at least one protrusion arranged at a second end and being at a right angle to said central shaft, said at least one protrusion being sized and shaped to be arranged within said first pocket or said second pocket and to magnetically interact with the at least one magnet arranged in said first or said second pocket.

By using the magnetic interaction of magnets located in pockets arranged along the longitudinal axis of the handle with the at least one protrusion, a very simple torque limiter is provided which essentially only includes two mono-block components which provide for a reliable cleaning and sterilization, especially since both the handle and the shaft may be easily disassembled prior to any cleaning or sterilization step. Further, by varying the interaction of the at least one protrusion with either said first or said second pocket, it is possible to adjust the torque level of the torque limiter by inserting the shaft turned by 180° into the handle. Hence, a very simple adjustment of the torque level is made possible.

Generally, the torque limiter is preferably used in relation to a surgical device, the device in particular being used for controlled insertion with measured tightening of implantable medical devices like bone screws, other threaded fixation devices or features in devices that need a rotational motion for locking or tightening, e.g. bayonet mechanisms.

A "pocket" as understood in the following application is a recess or clearance within the mono-block cylindrical handle-body. A pocket is delimited by a lower wall as well as a back wall arranged along said longitudinal axis of the cylindrical handle-body. Preferably, the handle-body and said first and second pockets are configured such that said pockets are also delimited by an upper wall, i.e. the pockets form recesses within said cylindrical handle-body. Said back walls are arranged parallel to the axis of said through bore, i.e. the axis of the through bore as well as the back walls of both pockets are arranged in a single line along said longitudinal axis of the cylindrical handle-body.

Both pockets are arranged on opposite sides of said cylindrical handle-body, i.e. both said pockets have back walls which are located along said longitudinal axis but which face away from each other. Arranged "along said longitudinal axis" means that said longitudinal axis is comprised in the back walls of said first and said second pocket.

In the following application, the term "mono-block" refers to any element made of a single piece or to an assembly of pieces having a common, completely closed outer surface. The feature "mono-block" in medical reusable instruments guarantees that no blood or tissue can get caught in small gaps, hinges or other features of the instrument, which may therefore be cleaned and sterilised in a far more optimal manner.

The term "right angle" is understood to encompass an angle of 90° as well as angles which are substantially 90°, i.e. having a maximal deviation of 5°, more preferably of 2°. Hence, the term "right angle" as used in the present application encompasses angles in the range of 85° to 95°, more preferably of 88° to 92°, most preferably however of exactly 90°.

Both said first and said second pockets intersect each other in the area of said through-bore, i.e. an open space is created in said area, linking said first and second pockets together. Preferably, an opening is provided in said cylindrical handle-body such that the shaft may be inserted into said through bore.

Preferably, said handle comprises one central through bore. However, in certain embodiments, the handle may comprise two or more through bores. The term "central" is understood to mean the location of the through bore on said longitudinal axis in an area in the centre of said handle.

The shaft is removably arranged in said through bore, i.e. said cylindrical handle-body and said shaft may be disassembled and assembled by insertion of the central shaft into said through bore.

The drive of the central shaft is configured to interact with a corresponding drive of an anchoring element, such as a bone screw. Preferably, said drive is configured as hexagonal or pentagonal drive. However, depending on the intended use of a surgical device with the inventive torque limiter other drive geometries may also be used. As a person having skill in the art will recognize, any handle may be used in connection with shafts having different drives.

The at least one magnet in said first pocket or in said second pocket preferably is a permanent magnet. More preferably, said at least one magnet is a samarium-cobalt magnet, a ferrite magnet or a neodymium magnet. Alternatively, said at least one magnet may be an electromagnet.

The at least one protrusion is sized and shaped to be arranged in either said first pocket or said second pocket and such as to magnetically interact with the at least one magnet. Preferably, said at least one protrusion is made of a paramagnetic material. Alternatively, said at least one protrusion may be made of a ferromagnetic material or said at least one protrusion may comprise at least one magnet which is arranged such as to cooperate with the at least one magnet in said first or said second pocket. Of course, in the case where said protrusion is ferromagnetic material or comprises at least one magnet, the polarity has to be chosen such that an attraction force is exerted between said at least one magnet in said first or said second pocket, i.e. the polarity of said at least one magnet in said first or said second pocket is opposite to said polarity of said ferromagnetic protrusion or said at least one magnet arranged on said at least one protrusion.

The cylindrical handle-body is preferably made of a polymer, more preferably of a biocompatible polymer. Said at least one magnet is arranged on a back wall of said first or said second pocket, preferably by means of gluing said at least one magnet into a recess formed on the back wall of said first or said second pocket. Most preferably, said at least one magnet is integrated into the back wall of said first or said second pocket by over moulding.

By means of the magnetic interaction between said at least one protrusion and said at least one magnet, a torque force may be transmitted from said handle to said shaft and subsequently to the drive arranged on the first end of the central shaft. If the torque force applied on said handle is greater than the magnetic attraction force between said at least one protrusion and said at least one magnet, the at least one protrusion will be disengaged from said at least one magnet and the transmission of the torque force from said handle to said shaft will be interrupted. The magnetic force exerted on said at least one protrusion by said at least one magnet depends on the magnetization of said at least one magnet as well as on the distance of said at least one magnet from the axis of the through bore along the longitudinal axis of the cylindrical handle body. As a person having skill in the art will recognize, the axis of the through bore acts as fulcrum and the at least one protrusion as lever and hence the relationship between said distance and the exerted force follows the law of the lever.

In the present application, the term "torque level" is used to define a specific torque force which corresponds to the value of the magnetic force exerted by the totality of the magnets onto said at least one protrusion. In the case where said torque force is exceeded, the magnetic force will no longer be sufficient to couple the rotation of the handle to the shaft and the protrusions will be released from the two pockets.

Preferably, said shaft comprises a first protrusion and a second protrusion arranged at a right angle to said central shaft and at an angle of 180° relative to each other. Hence, once the shaft is arranged in said handle, i.e. the central shaft is inserted into said through bore, one protrusion is arranged in each of said first and said second pocket. As a person having skill in the art will recognize, a shaft with two protrusions arranged at an angle of 180° to each other may be arranged in a handle in two different directions. In a first direction, the first protrusion is arranged in said first pocket while the second protrusion is arranged in said second pocket. In a second direction, said first protrusion is arranged in said second pocket while the second protrusion is arranged in said first pocket.

Having two protrusions allows to increase the torque level of the inventive torque limiter, as the at least one magnet of both said first pocket and said second pocket will exert a magnetic force onto said two protrusions.

The first protrusion and the second protrusion are preferably of different lengths. This allows providing for different torque levels depending on the direction the shaft is arranged in the handle. For example, in the case where the first protrusion is longer as the second protrusion and the shaft is arranged in the handle in a first orientation, where said first protrusion is arranged in said first pocket, said first protrusion may interact with the at least one magnet arranged in said first pocket. However, when the shaft is arranged in said handle in a second orientation where the second, shorter protrusion is arranged in said first pocket, the second protrusion does not span a sufficient length of said pocket to interact with the at least one magnet in said pocket. Hence, no magnetic force will be exerted by the at least one magnet in said first pocket onto said second protrusion. Therefore, the resulting total magnetic force exerted onto said two protrusions varies depending on the orientation said shaft is arranged in said handle, thus allowing to vary the torque level to two different values with a single handle and shaft.

Alternatively, said shaft may also comprise more than two protrusions, such as e.g. four protrusions, which preferably have different lengths and which are arranged at a right angle relative to each other. Hence, such a shaft may be arranged in four different orientations in a handle, each orientation may yield a different torque level to the torque limiter.

Preferably, said at least one magnet in said first pocket has a different magnetization as the at least one magnet in said second pocket. In the present application, the term "different magnetization" means that said magnets have a different density of magnetic moments. Hence, depending on the pocket said at least one protrusion is arranged, a different magnetic force will be exerted on said at least one protrusion. In the case where any of said first pocket or said second pocket includes more than one magnet, the magnets arranged in the same pocket preferably also have a different magnetization.

Said at least one magnet in said first pocket is preferably located at a different distance from the axis of said central through bore along the longitudinal axis of the cylindrical handle-body than said at least one magnet in said second pocket.

Hence, depending on the pocket the at least one protrusion is arranged in, a different force will be exerted thereon, following the law of the lever. This allows the generation of different torque levels even when using magnets having the same magnetization for both said first and said second pockets, as the force exerted onto said at least one protrusion increases with increasing distance of said at least one magnet from the axis of said through bore.

In the case where a shaft having two protrusions having different lengths is used, the variation of the distance of the at least one magnet from the axis of the through bore in each of the pockets may be used to vary the magnetic force exerted on said protrusions depending on the orientation said shaft is inserted into said handle. E.g. a longer protrusion may interact with the at least one magnet in the first pocket, while a shorter protrusion will not reach to said at least one magnet and hence not magnetically interact therewith.

Preferably, said first pocket and said second pocket comprise a different number of magnets.

This allows a further variation of the magnetic forces exerted on said at least one protrusion in each of said first pocket and said second pocket. Especially in connection with a shaft having two protrusions with different lengths, each of said protrusions may interact with a different number of magnets depending on the insertion orientation of said shaft. E.g. a shorter protrusion may interact with only one magnet in the first pocket, while the longer protrusion may interact with two or more magnets in the same pocket. Hence, depending on whether the shaft is inserted into said handle such that the shorter or the longer protrusion will be arranged in said first pocket, different magnetic forces will be exerted on said shorter or said longer protrusion.

Preferably, said handle comprises at least one second central through bore arranged adjacent said central through bore along said longitudinal axis. Provision of at least one second central through bore allows arranging the shaft in at least two different positions within the handle. Especially in conjunction with a shaft having two protrusions with different lengths a further variation of the exerted magnetic forces is made possible as the protrusions will interact with a different number of magnets depending on the through bore the central shaft is inserted in. Preferably, the handle comprises two through bores, i.e. the central through bore as well as one second through bore. However, in certain embodiments, the handle may comprise more through bores, such as three, four or more through bores.

Preferably, said at least one magnet in said first pocket and/or in said second pocket is slidable along said longitudinal axis. Having a slidable magnet allows to vary the torque level by changing the distance of said at least one magnet to the axis of the through bore. Preferably, the slidable magnet is arranged on a support which is linearly movable along the longitudinal axis of said cylindrical handle-body. Further preferably, the cylindrical handle-body comprises several pre-defined positions in which it may be fixated, each position corresponding to a defined torque level.

The present invention also relates to a kit comprising at least one handle and at least two shafts as described above. Providing a kit with several different shafts, which preferably have protrusions with different lengths, allows e.g. a surgeon to choose among a wide variety of different torque levels according to the specific torque needed for the task at hand. Preferably, said kit also comprises two or more different handles, each handle having varying numbers of magnets, different positions of magnet within said two pockets and/or varying magnetizations.

Other advantageous embodiments and combinations of features come out from the detailed description below and the totality of the claims.

BRIEF DESCRIPTION OF THE DRAWINGS

The drawings used to explain the embodiments show:

FIGS. 4a-4c assembly steps between the handle according to FIGS. 1a and 1b and a shaft according to FIG. 3a;

In the figures, the same components are given the same reference symbols.

Preferred Embodiments

Figure 1A:
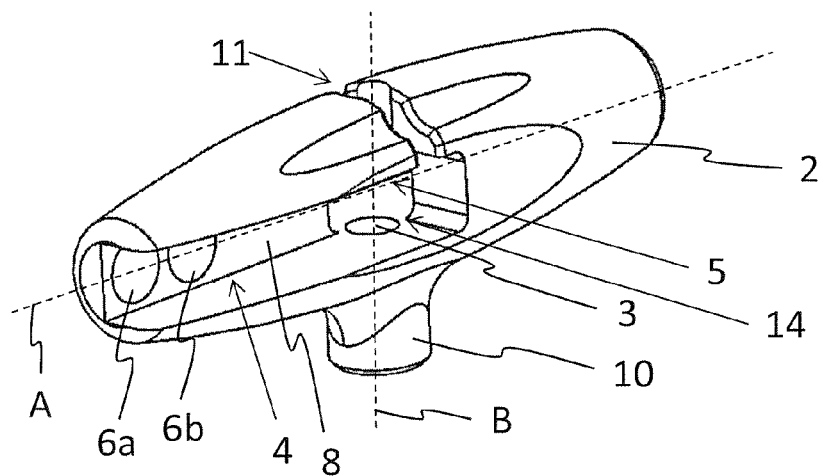
FIGS. 1a, 1b A mono-block handle for a torque limiter according to the present invention.

FIG. 1a shows a mono-block handle 2 of a torque limiter according to the present invention. The handle 2 has a cylindrical handle body for holding and manipulation, the handle 2 comprising a central through bore 3 for insertion of a shaft. The axis B of said through bore 3 is at a right angle to a longitudinal axis A of said cylindrical handle-body. Furthermore, the body 2 features a first pocket 4 and a second pocket 5 arranged on different sides of the handle 2 and along the longitudinal axis A of said cylindrical handle body. The first pocket comprises a first magnet 6a and a second magnet 6b while the second pocket 5 comprises a third magnet 7a and a fourth magnet 7b (the third and fourth magnets 7a, 7b of the second pocket 5 are hidden by the cylindrical handle-body in FIG. 1a). The magnets 6a, 6b, 7a, 7b are arranged in recesses provided on a back wall 8, 9 of said pockets 4, 5. The back wall 8, 9 of each of said first pocket 4 and said second pocket 5 is arranged along the longitudinal axis A of said cylindrical handle-body. The first pocket 4 and the second pocket 5 intersect each other in an area around the through bore 3, hence creating an open space 14 linking said first pocket 4 with said second pocket 5. In the area of said open space 14, an opening 11 is provided to allow the insertion of a shaft having at least one protrusion into said handle 2. The opening 11 is generally shaped as a slit spanning in a direction which is orthogonal to the axis B of the through bore 3 and the longitudinal axis A of the cylindrical handle-body, i.e. allowing an insertion of a shaft with at least one protrusion in an orientation where said at least one protrusion is pointing in the direction of the opening 11. Further, the handle includes a nose 10 extending around the axis B of said through bore 3 on the side opposite said opening 11. The nose 10 helps to keep a shaft inserted into the central through bore 3 to stay aligned with the axis B of said central through bore 3.

Figure 1B:
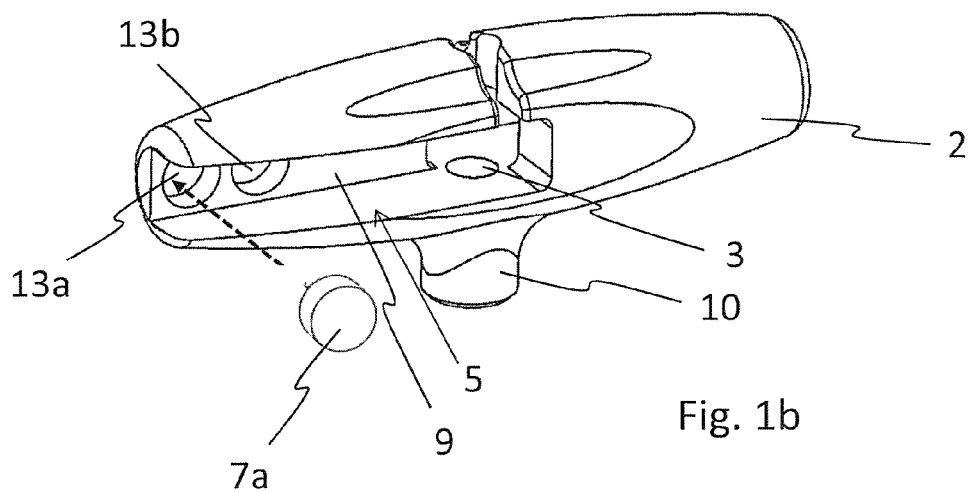

FIG. 1b shows the handle 2 according to FIG. 1a turned by approximately 180° around the axis B of the central through bore 3. It may be recognized that both the first pocket 4 and the second pocket 5 are identical in respect to their dimension and arrangement along said longitudinal axis A, with the only difference being the side of the handle 2 they lay on. In the embodiment as shown, the arrangement of the third magnet 7a and the fourth magnet 7b of the second pocket 5 is identical to the arrangement of the first magnet 6a and the second magnet 6b of the first pocket 4. In FIG. 1b, a third recess 13a and a fourth recess 13b may be seen. The third magnet 7a and the fourth magnet 7b (not shown) are mounted into said third recess 13a and said fourth recess 13b. The recesses 13a, 13b are sized such that the magnets 7a, 7b snuggly fit into, such that the handle 2 keeps a mono-block structure.

Figure 2:
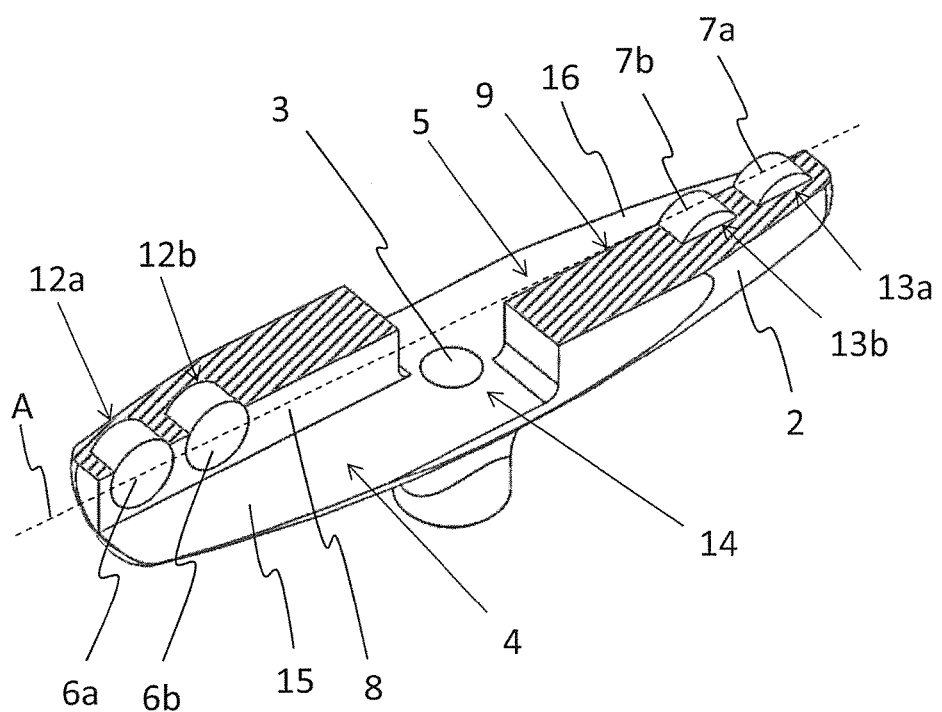
FIG. 2a sectional cut of the handle according to FIGS. 1a and 1b.

FIG. 2 shows the handle 2 according to FIGS. 1a and 1b in a sectional cut. The integration of the magnets 6a, 6b, 7a, 7b into corresponding recesses 12a, 12b, 13a, 13b arranged on the respective back walls 8, 9 of said first pocket 4 and said second pocket 5 are recognizable. The fixation of the magnets 6a, 6b, 7a, 7b into any of the recesses 12a, 12b 13a, 13b can be by gluing, welding, integration in a welded cover, fixation by over-moulding techniques, and etcetera. The intersection of said first pocket 4 and said second pocket 5 creates an open space 14 around the central through bore 3. Further, as may be recognized, the first pocket 4 is delimited by a first lower wall 15 and a first back wall 8. Likewise, the second pocket 5 is delimited by a second lower wall 16 and a second back wall 9. A further delimitation of said pockets 4, 5 is an upper wall which is arranged parallel to said lower walls 15, 16. However, said upper walls are not shown in FIG. 2, since they are arranged above the cutting plane.

Figure 3A:
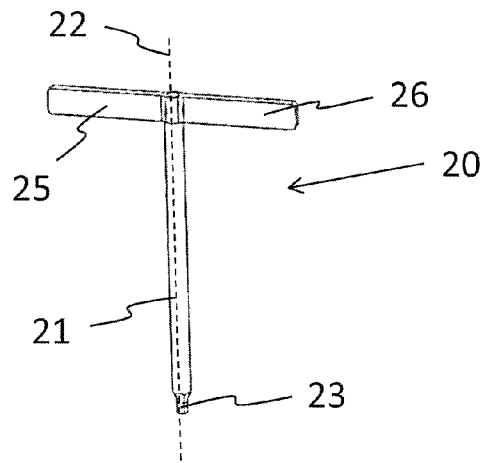
FIGS. 3a-3c different shafts for a torque limiter according to the present invention.
Figure 3B:
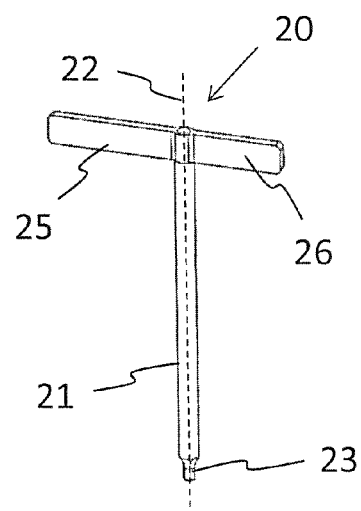
Figure 3C:
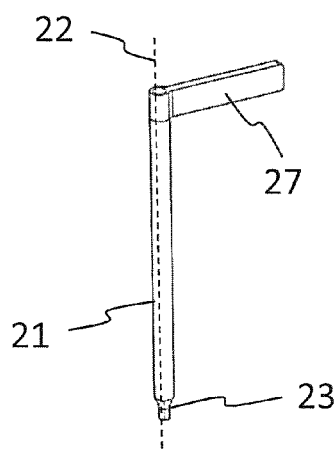

Referring to FIGS. 3a to 3c, a number of different mono-block shafts 20 are shown. Once arranged in the handle 2, the shaft 20 transfers manually applied torque to a target device which is to be tightened or screwed in. All variants of shaft 20 comprise a central shaft 21 with a drive 22 at a first end as well as either two protrusions 25, 26 (FIGS. 3a, 3b) or only one protrusion 27 (FIG. 3c) arranged on a second end and extending in a direction which is perpendicular to a central axis 22 of said central shaft 21. The protrusions 25, 26, 27 have a generally rectangular shape which is dimensioned to fit into the pockets 4, 5 of a corresponding handle 2.

Shaft 20 according to FIG. 3a comprises a first protrusion 25 and a second protrusion 26 of equal length, while the first protrusion 25 of the shaft 20 according to FIG. 3b is longer than the second protrusion 26. The protrusions 25, 26 of the shafts 21 according to FIGS. 3a and 3b have an angle of 180° relative to each other. The shaft 21 according to FIG. 3c only comprises a single protrusion 27.

The drive 22 in FIGS. 3a to 3d is a hexagonal drive. However, the drive 22 may comprise any drive type suitable for its specific application.

Figure 4A:
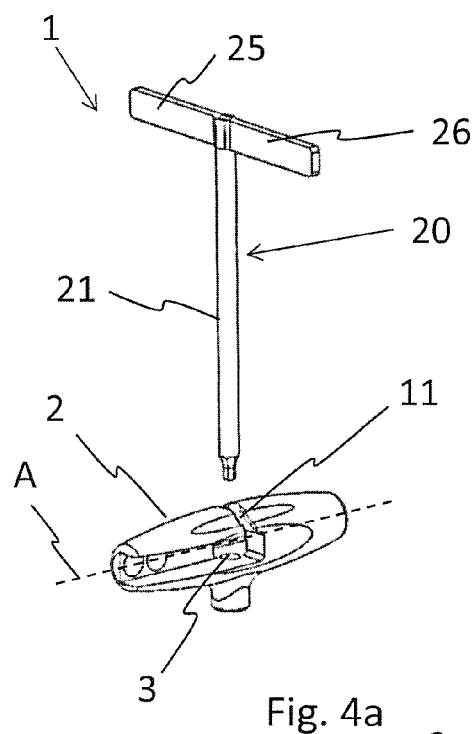
Figure 4B:
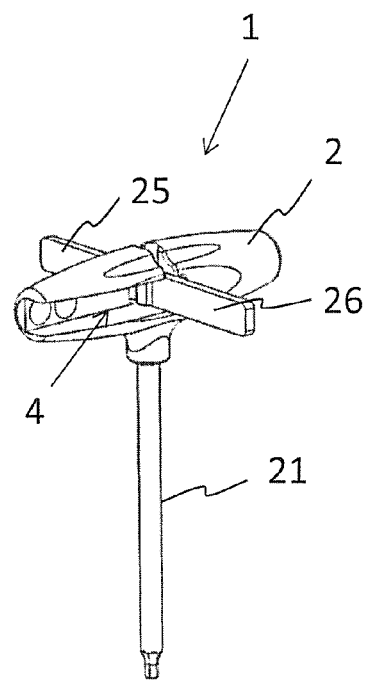
Figure 4C:
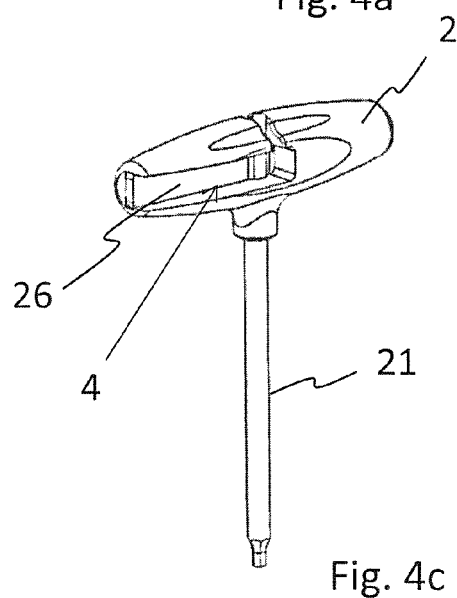

Referring to FIGS. 4a to 4c, the assembly steps between the handle 2 as shown in FIGS. 1a and 1b and the shaft 20 according to FIG. 3a are shown. In a first step, the shaft 20 is inserted into the handle 2 with the central shaft 21 aligning into the central through bore 3. The protrusions 25, 26 are oriented substantially perpendicular to the longitudinal axis A of the handle 2 such that the protrusions 25, 26 pass through the opening 11 of the handle 2.

In a further step, referring to FIG. 4b, after reaching a first end position the shaft 20 is rotated clock-wise until the protrusions 25, 26 are arranged within the two pockets 4, 5 and interact with the magnets 6a, 6b, 7a, 7b in its final end position, which is shown in FIG. 4c.

Figure 5A:
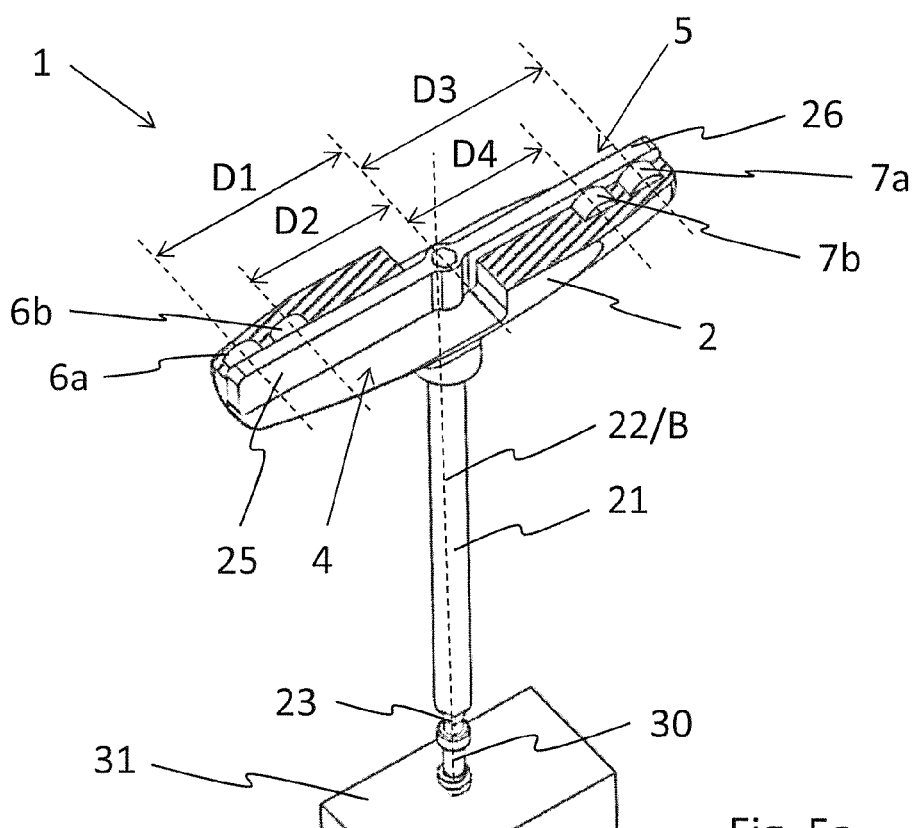
FIGS. 5a, 5b a sectional cut of a first embodiment of a torque limiter according to the present invention.
Figure 5B:
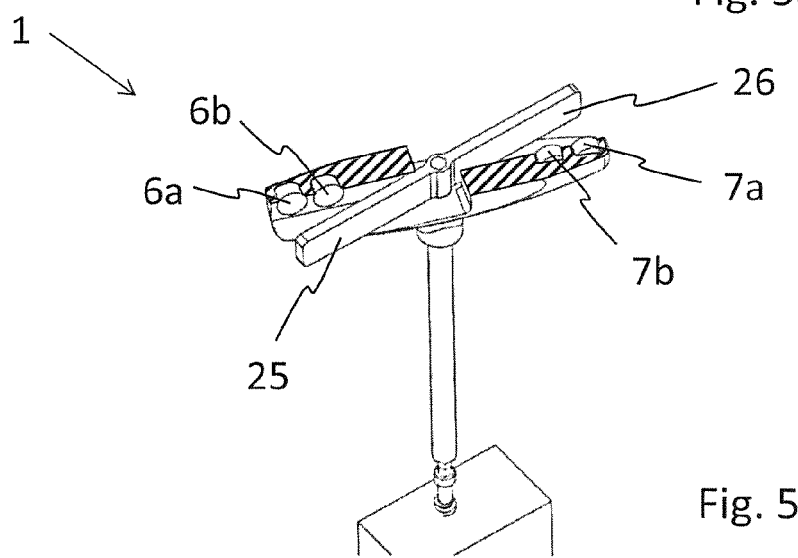

Referring to FIGS. 5a and 5b, while holding the handle 2, a user would rotate the handle 2 clock-wise to create a torque about the axis 22 of the central shaft 21, e.g. to insert a screw 30 in an object 31. The handle 2 transfers the torque to the central shaft 21 via the magnetic force exerted by the magnets 6a, 6b, 7a, 7b onto the two protrusions 25, 26. This exerted magnetic force is resisting a first torque level. Said exerted force corresponds to the multiplication of the magnetization of each of the magnets 6a, 6b, 7a, 7b times the distances D1, D2, D3, D4 between each of the magnets 6a, 6b, 7a, 7b and the axis B of said central through bore 3. The axis B of the central through bore 3 is identical with the central axis 22 of the central shaft 21, as said central shaft 21 is inserted into said trough bore 3. Exemplary for the torque limiter as shown in FIGS. 5a and 5b, the exerted magnetic force of magnets 6a, 6b, 7a, 7b is:

Exerted force=((Magnetization first magnet 6a×D1)+ (Magnetization second magnet 6b×D2)+(Magnetization third magnet 7a×D3)+(Magnetization fourth magnet 7b×D4))

When the torque level applied to the handle 2 by the hand of the user is exceeding the exerted force, the protrusions 25, 26 will disengage from the magnets 6a, 6b, 7a, 7b and indicate that the torque level was reached, as illustrated in FIG. 5b.

Shaft 20 can be arranged in handle 2 in two orientations, 180° rotationally offset. In the example of FIGS. 5a and 5b, both protrusions 25, 26 of the shaft 20 interact with all the magnets 6a, 6b, 7a, 7b in both assembly configurations. Therefore, for the torque limiter 1 according to this embodiment, the torque level is equal for both insertion orientations.

Figure 6:
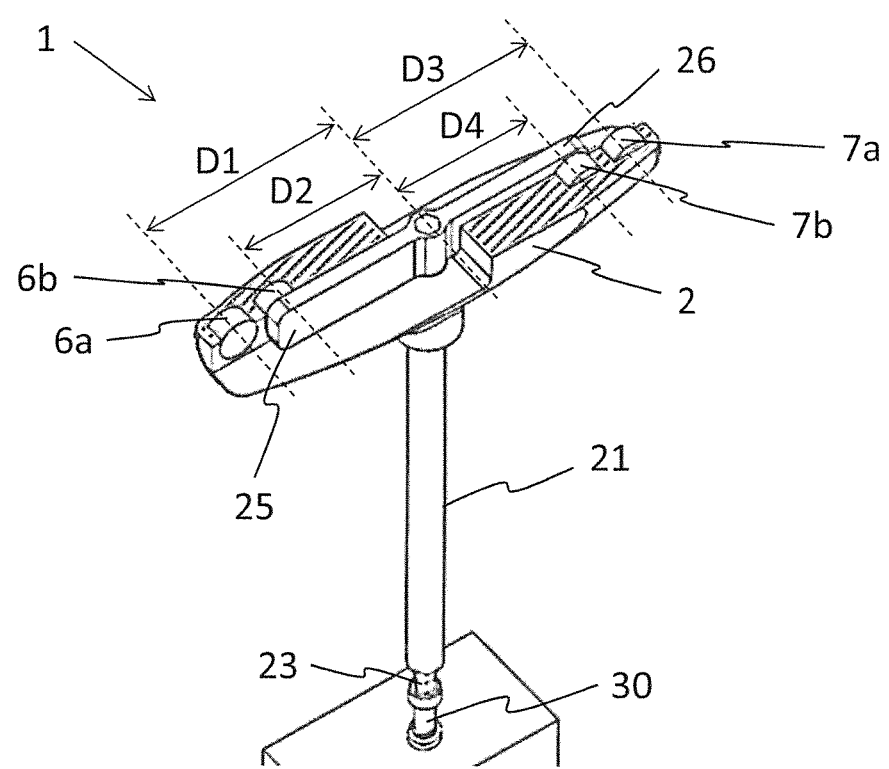
FIG. 6 a sectional cut of a second embodiment of a torque limiter.

FIG. 6 shows a second embodiment of a torque limiter 1. The protrusions 25, 26 of shaft 21 only interact with the second magnet 6b and the fourth magnet 7b, while the length of both protrusions 25, 26 is not sufficient to allow an interaction with the first magnet 6a or the third magnet 7a. The torque level of this embodiment equals the exerted force which is the sum of the force-distance pairs:

Exerted force=((Magnetization second magnet 6b×D2)+(Magnetization third magnet 7b×D3))

With this system a torque limiter kit can comprise one single handle 2 with multiple shafts 20, each shaft 20 yielding an individual torque level when arranged in said handle 2.

Figure 7A:
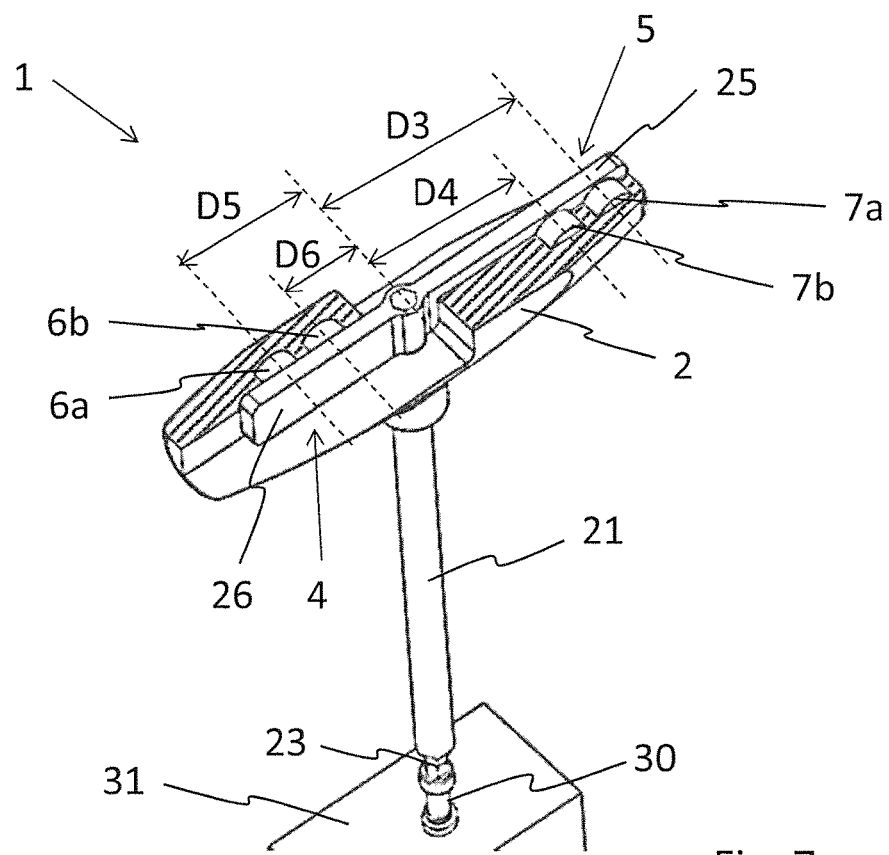
FIGS. 7a-7c a sectional cut of a third embodiment of a torque limiter.
Figure 7B:
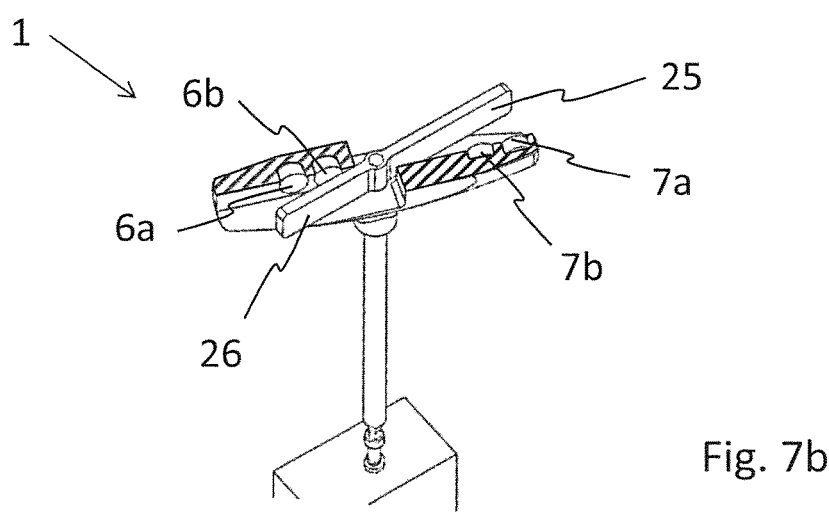
Figure 7C:
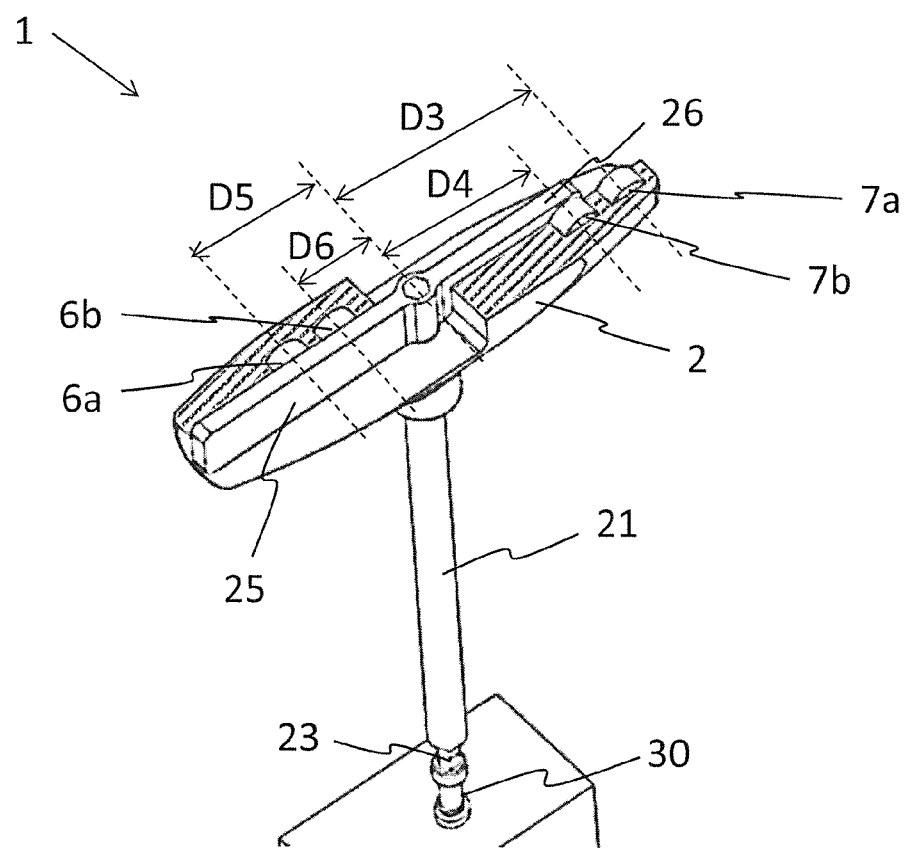

Referring to FIGS. 7a to 7c, a third embodiment of a torque limiter 1 according to the present invention is shown. The first protrusion 25 of the shaft 20 has a greater length than the second protrusion 26. Further, the first magnet 6a and the second magnet 6b are arranged at different distances D5, D6 compared to the distances D1, D2 according to the embodiment as shown in FIGS. 5a and 5b.

The force exerted by the magnets 6a, 6b, 7a, 7b onto said two protrusions 25, 26 is based on the multiplication of the magnetization of each magnet 6a, 6b, 7a, 7b and the distance between the corresponding magnet 6a, 6b, 7a, 7b and the axis B of the central through bore 3. FIG. 7a shows the arrangement of the shaft 20 in handle 2 in a first orientation, where the first protrusion 25 is arranged in the first pocket 4 and the second protrusion 26 is arranged in the second pocket 5. The exerted force is given by:

Exerted force=((Magnetization first magnet 6a×D5)+ (Magnetization second magnet 6b×D6)+(Magnetization third magnet 7a×D3)+(Magnetization fourth magnet 7b×D4))

FIG. 7b shows the situation when the torque applied to the handle 2 is higher than the exerted force. In this case, which corresponds to the situation as shown in FIG. 5b, the two protrusions 25, 26 will disengage from the two pockets 4, 5.

Now, when the shaft 20 is arranged in the handle 2 in a second orientation, as shown in FIG. 7c, the torque limiter comprises a second torque level, since due to the shorter length of the second protrusion 26, the second protrusion 26 does not magnetically interact with the third magnet 7a of the second pocket 5. Hence, the exerted force is smaller than in the first configuration, thus giving the torque limiter 1 a second torque level:

Exerted force=((Magnetization first magnet 6a×D5)+ (Magnetization second magnet 6b×D6)+(Magnetization fourth magnet 7b×D4))

This torque limiter 1 according to this embodiment comprises one handle 2 and one shaft 20 which may be assembled in two different orientations, resulting in two different torque levels.

Figure 8A:
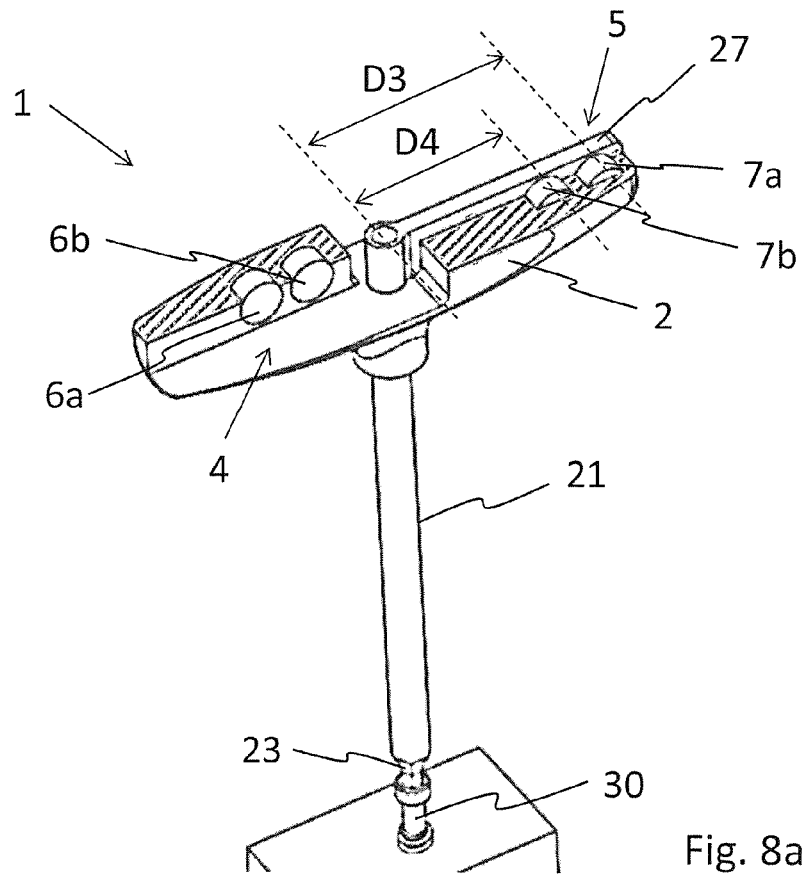
FIGS. 8a-8c a sectional cut of a fourth embodiment of a torque limiter.
Figure 8B:
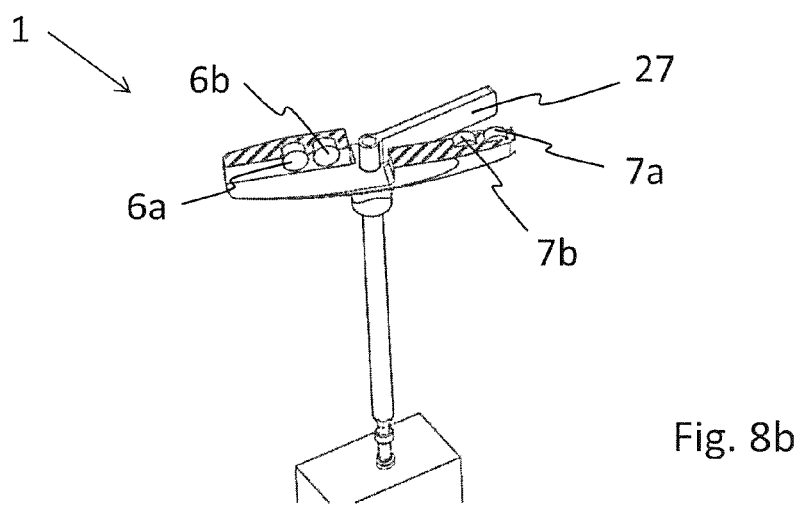
Figure 8C:
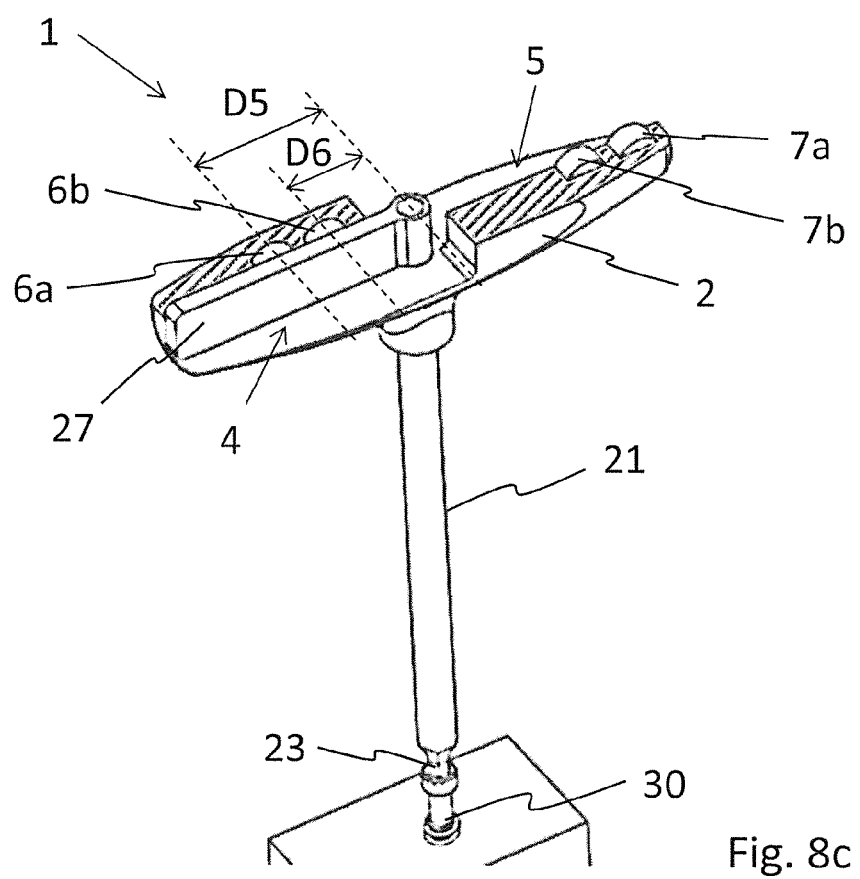

FIGS. 8a to 8c show a further embodiment of a torque limiter 1 according to the present invention. Contrary to the embodiments as shown in the previous figures, the shaft 20 of this embodiment only comprises one single protrusion 27. The handle 2 corresponds to the handle of the embodiment as shown in FIGS. 7a to 7c.

FIG. 8a shows this embodiment with the shaft arranged in a first orientation. Thereby, the single protrusion 27 magnetically interacts with the third magnet 7a and the fourth magnet 7b of the second pocket 5. The second orientation is shown in FIG. 7c. In this second orientation, the single protrusion 27 magnetically interacts with the first magnet 6a and the second magnet 6b of the first pocket 4.

In the first assembly configuration, the exerted force equals to:

Exerted force 1=((Magnetization third magnet 7a×D3)+(Magnetization fourth magnet 7b×D4))

In the second assembly configuration, the system comprises a second exerted force:

Exerted force 2=((Magnetization first magnet 6a×D1)+(Magnetization second magnet 6b×D2))

FIG. 8b shows the situation where the torque exerted on the handle 2 is greater than the force exerted by the third magnet 7a and the fourth magnet 7b onto both protrusions 25, 26, i.e. when the torque level for the first orientation is reached and the two protrusions 25, 26 disengage from the two pockets 4, 5.

Hence, this embodiment of torque limiter 1 comprises one handle 2 and one shaft 20 that can be assembled in two different orientations, resulting in two different torque levels.

Figure 9:
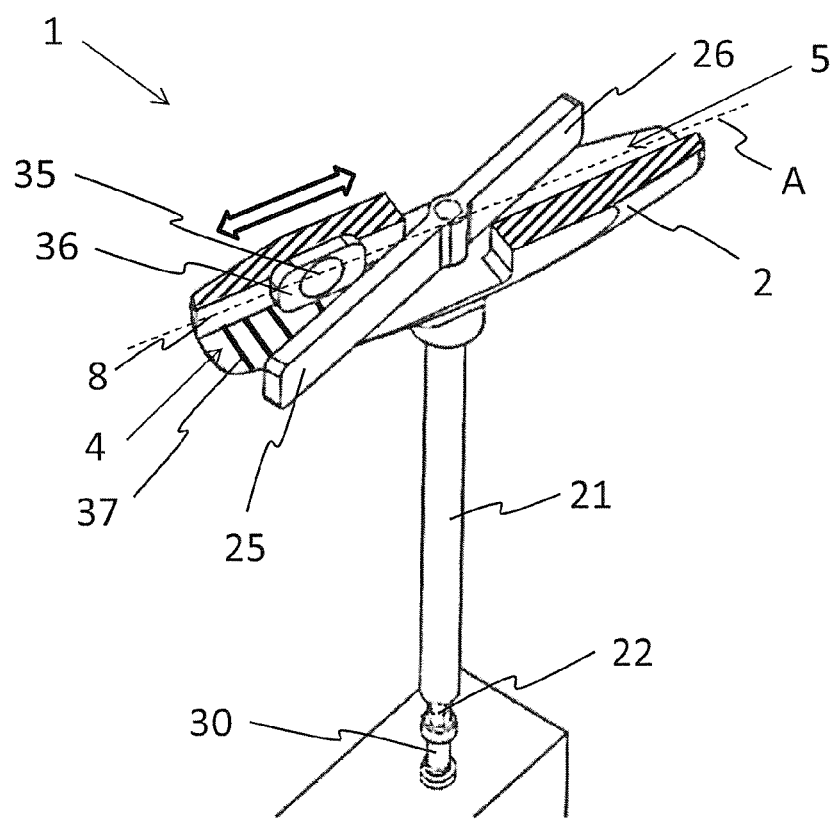
FIG. 9 a sectional cut of an alternative embodiment of a torque limiter.

FIG. 9 shows an alternative embodiment of the torque limiter 1 according to the present invention. The handle 2 comprises a movable magnet 35 which may be linearly moved within the handle 2 along said longitudinal axis A such as to vary the distance from the movable magnet 35 to the axis of the central through bore 3. Linear movement of the movable magnet 35 allows setting different torque levels. In the embodiment shown, the movable magnet 35 is arranged on a support 36 which may be linearly translated along the longitudinal axis A.

Figure 10A:
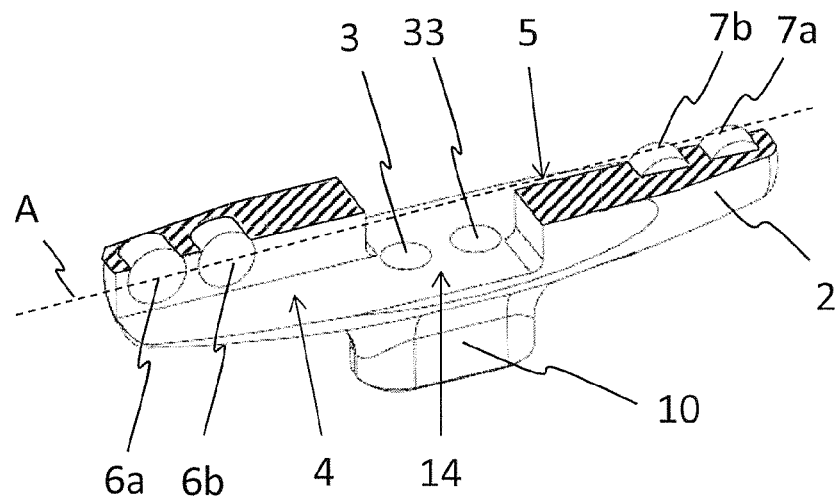
FIGS. 10a-10c a further embodiment of a torque limiter with two through bores in the handle.
Figure 10B:
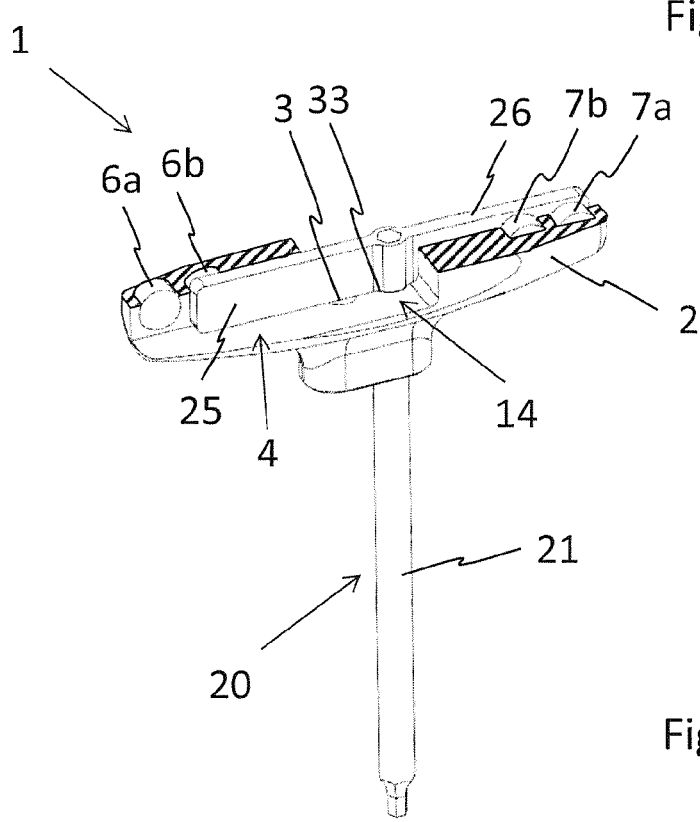
Figure 10C:
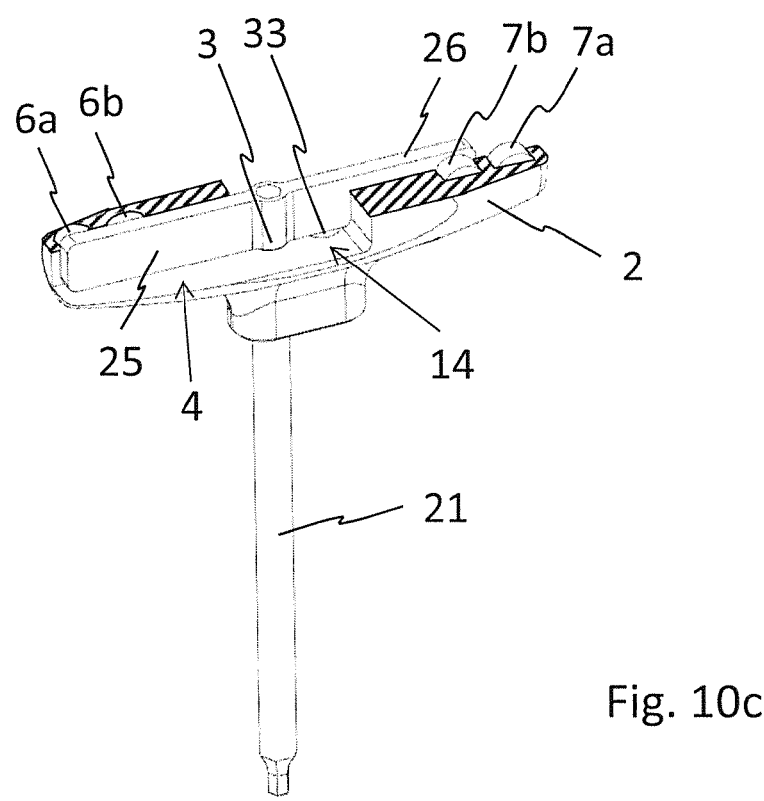

FIGS. 10a to 10c show a further embodiment of a torque limiter 1 according to the present invention. As shown in FIG. 10a, which is a sectional view of the handle 2, the handle 2 according to this embodiment comprises an additional second through bore 33 arranged adjacent said central through bore 3 along said longitudinal axis A. Otherwise, the handle 2 corresponds to the embodiment as shown in FIGS. 1a and 1b.

FIG. 10b depicts the torque limiter 1 in a first configuration, where the central shaft 21 of shaft 20 is arranged in said second through bore 33. In this configuration, the first protrusion 25 which is arranged in said first pocket 4 only magnetically interacts with the second magnet 6b, while the second protrusion 26 magnetically interacts with the third magnet 7a and the fourth magnet 7b.

FIG. 10c shows the torque limiter 1 in a second embodiment, where the central shaft 21 of shaft 20 is arranged in said central through bore 3. In this configuration, the first protrusion 25 now magnetically interacts with the first magnet 6a and the second magnet 6b, while the second protrusion 26 only interacts with the fourth magnet 26. Hence, depending on the arrangement of the central shaft 21 in the central through bore 3 or the second through bore 33, different magnetic forces exerted onto said protrusions 25, 26 may be achieved. In a further variation, using a shaft 20 having protrusions 25, 26 with different lengths allow to further vary the exerted magnetic force.

The invention claimed is:

1. A torque limiter comprising a handle having a mono-block cylindrical handle-body, said cylindrical handle-body comprising a central through bore having an axis at a right angle to a longitudinal axis of the cylindrical handle-body, a first pocket and a second pocket, said first pocket being arranged on a first side and said second pocket being arranged on a second side of said cylindrical handle-body opposite of said first side, the first pocket and the second pocket being arranged along said longitudinal axis and intersecting each other in the area of said central through bore, each of said first pocket and said second pocket comprising at least one magnet, the torque limiter further comprising a mono-block shaft having a central shaft removably arranged in said central through bore, said central shaft having a drive arranged at a first end, wherein the central shaft comprises at least one protrusion arranged at a second end and being at a right angle to a central axis of said central shaft, said at least one protrusion being sized and shaped to be arranged within said first pocket or said second pocket and to magnetically interact with the at least one magnet arranged in said first pocket or said second pocket, the central axis being at a right angle to the longitudinal axis of the handle-body, the first pocket and the second pocket forming a first recess, and a second, different recess, respectively, within the handle-body such that the first recess extends from the area of said central through bore in a first direction, while the second recess extends from the area of said central through bore in a second, opposite direction, the first and second directions being parallel to the longitudinal axis of the handle-body, the first recess and the second recess being delimited by at least a first back wall and a second back wall, respectively, such that the first back wall faces in a first direction, while the second back wall faces in a second, opposite direction, each of the first and second back walls comprising the at least one magnet, the first and second back walls extending substantially along the longitudinal axis of the handle-body, the first and second recesses being devoid of a front wall substantially parallel to the first and second back walls.

2. The torque limiter according to claim 1, wherein said shaft comprises a first protrusion and a second protrusion arranged at a right angle to said central axis and at an angle of 180° relative to each other.

3. The torque limiter according to claim 2, wherein said first protrusion and said second protrusion are of different lengths.

4. The torque limiter according to claim 1, wherein the at least one magnet in said first pocket has a different magnetization as the at least one magnet in said second pocket.

5. The torque limiter according to claim 1, wherein said at least one magnet in said first pocket is located at a different distance from the axis of said central through bore along the longitudinal axis of the cylindrical handle-body than said at least one magnet in said second pocket.

6. The torque limiter according to claim 1, wherein said first pocket and said second pocket comprise a different number of magnets.

7. The torque limiter according to claim 1, wherein said handle comprises at least one second central through bore arranged adjacent said central through bore along said longitudinal axis.

8. The torque limiter according to claim 1, wherein said at least one magnet in said first pocket and/or in said second pocket is slidable along said longitudinal axis.

9. A kit comprising at least one handle and at least two shafts of a torque limiter according to claim 1.

10. A torque limiter comprising:
a handle having a first end and a second end defining a longitudinal axis, a central through-bore having an axis perpendicular to the longitudinal axis, a center plane defined by the longitudinal axis and the axis of the central through-bore, the center plane having a first side and a second side, the handle further having two pockets, a first pocket located at the first end and positioned on the first side of the center plane, a second pocket located at the second end and positioned on the second side of the center plane, a first magnet arrangement at the first end and positioned near the first pocket, and a second magnet arrangement on the second end and positioned near the second pocket; and
a shaft having a central shaft removably inserted into the central through-bore, and at least one protrusion extending from the central shaft at a right angle, the at least one protrusion removably inserted into the first pocket or the second and magnetically engaged with the first magnetic arrangement or the second magnetic arrangement,
wherein the handle is configured such that when the at least one protrusion of the shaft is inserted into the first pocket and the handle is rotated about the central shaft in a first direction, the at least one protrusion will disengage from the first magnetic arrangement, first pocket and handle to limit torsion about the central shaft, and wherein the handle is configured such that when the at least one protrusion of the shaft is inserted into the second pocket and the handle is rotated about the central shaft in the first direction, the at least one protrusion will disengage from the second magnetic arrangement, second pocket and handle to limit torsion about the central shaft, and wherein the handle is configured such that when the at least one protrusion of the shaft is inserted into the first pocket or the second pocket and the handle is rotated about the central shaft in a second direction, opposite of the first direction, torsion about the central shaft will not be limited.

11. The torque limiter of claim 10, wherein the first magnetic arrangement has a larger gaussian value than the second magnetic arrangement.

12. The torque limiter of claim 10, further comprising an adjacent through-bore, adjacent to the central through-bore and positioned on the longitudinal axis.

13. The torque limiter of claim 10, wherein the first magnetic arrangement is comprised of one magnet and is located a greater distance from the central through-bore than the second magnetic arrangement.

14. The torque limiter of claim 11, wherein the first magnetic arrangement has a gaussian value equal to a gaussian value the second magnetic arrangement.

15. A torque limiter comprising:
a handle having a first end and a second end defining a longitudinal axis, a central through-bore having an axis perpendicular to the longitudinal axis, a center plane defined by the longitudinal axis having a first side and a second side, a first pocket located at the first end and positioned on the first side of the center plane, a second pocket located at the second end and positioned on the second side of the center plane, a first magnet arrangement at the first end and positioned on the second side of the center plane, and a second magnet arrangement on the second end and the first side of the center plane; and a shaft having a central shaft removably inserted into the central through-bore, a first protrusion extending from the shaft at a right angle, the first protrusion removably inserted into the first pocket and magnetically engaged with the first magnetic arrangement, and a second protrusion extending from the shaft at a right angle and in a direction opposing the first protrusion, the second protrusion removably inserted into the second pocket of the handle and magnetically engaged with the second magnetic arrangement, the first pocket and the second pockets being delimited by at least a first back wall and a second back wall, respectively, the first back wall provided on the first side of the center plane and the second back wall provided on the second side of the center plane, the first and second back walls extending substantially along the longitudinal axis of the handle-body, the first and second pockets being devoid of a front wall substantially parallel to the first and second back walls.

16. The torque limiter of 15, wherein the first protrusion of the shaft and the second protrusion of the shaft are provided with different lengths.

17. The torque limiter of claim 15, wherein the first magnetic arrangement has a larger gaussian value than the second magnetic arrangement.

18. The torque limiter of claim 15, further comprising an adjacent through-bore, adjacent to the central through-bore and positioned on the longitudinal axis.

19. The torque limiter of claim 15, wherein the first magnetic arrangement magnet is located a greater distance from the central through-bore than the second magnetic arrangement.

20. The torque limiter of claim 19, wherein the first magnetic arrangement has a gaussian value equal to a gaussian value the second magnetic arrangement.

* * * * *